United States Patent [19]
Czekai et al.

[11] Patent Number: 5,862,999
[45] Date of Patent: Jan. 26, 1999

[54] METHOD OF GRINDING PHARMACEUTICAL SUBSTANCES

[75] Inventors: David A. Czekai, Honeoye Falls; Larry P. Seaman, Mount Morris, both of N.Y.

[73] Assignee: Nano Systems L.L.C., King of Prussia, Pa.

[21] Appl. No.: 491,539

[22] Filed: Jun. 15, 1995

Related U.S. Application Data

[63] Continuation of Ser. No. 249,781, May 25, 1994, abandoned.
[51] Int. Cl.$^6$ .................................................. B02C 17/16
[52] U.S. Cl. ................................. 241/21; 241/24
[58] Field of Search .................................. 241/5, 21, 22, 241/30, 24, 29, 170–183, 184

[56] References Cited

U.S. PATENT DOCUMENTS 5,320,284  6/1994  Nishida et al. ........................... 241/21

FOREIGN PATENT DOCUMENTS 247895  12/1987  European Pat. Off. ............... 241/184
273210  11/1989  Germany ................................. 241/184
197711  11/1977  U.S.S.R. ................................. 241/184
580211  11/1977  U.S.S.R. ................................. 241/184

*Primary Examiner*—Timothy V. Eley
*Attorney, Agent, or Firm*—Foley & Lardner

[57] ABSTRACT

A method of preparing submicron particles of a therapeutic or diagnostic agent which comprises grinding the agent in the presence of grinding media having a mean particle size of less than about 75 microns. In a preferred embodiment, the grinding media is a polymeric resin. The method provides extremely fine particles, e.g., less than 100 nanometers in size, free of unacceptable contamination.

26 Claims, No Drawings

METHOD OF GRINDING PHARMACEUTICAL SUBSTANCES

This is a Continuation of application U.S. Ser. No. 08/249,789, filed 25 May, 1994 now abandoned.

BACKGROUND OF THE INVENTION

Various grinding media, such as stainless steel, zirconium silicate, zirconium oxide, glass, and the like, typically in the form of spherical beads, are commonly used in various mills, including media mills, for grinding materials. Heretofore, efforts have been made to control the size and size range of drug particles in pharmaceutical compositions by a variety of methods, including various milling techniques, such as airjet milling and wet milling. However, there tends to be a bias in the pharmaceutical arts against milling techniques, particularly wet milling, due to concerns associated with contamination. For example, in the preparation of pharmaceuticals for oral and parenteral applications, it is desirable to have total contamination, e.g., of heavy metals, below about 10 parts per million. The need to control and minimize contamination is particularly critical in the milling of parenteral products due to potential safety issues associated with injection of contaminants.

Liversidge et al, U.S. Pat. No. 5,145,684, and European Patent Application 498,492, describe dispersible particles consisting of a drug substance or an x-ray contrast agent having a surface modifier adsorbed on the surface thereof in an amount sufficient to maintain an effective average particle size of less than about 400 nm. The particles are prepared by dispersing a drug substance or imaging agent in a liquid dispersion medium and wet grinding in the presence of rigid grinding media.

Bruno et al, commonly-owned U.S. patent application Ser. No. 07/981,639 filed Nov. 25, 1992 entitled *Method for Grinding Pharmaceutical Substances* discloses polymeric grinding media for fine grinding pharmaceutical compositions. Bruno et al disclose that the media can be in the size range of 0.1–3 mm (100–3000 microns). The media specifically exemplified in the working examples have a mean particle size in the range of 0.3–0.6 mm (300–600 microns).

In practicing the methods described by Liversidge et al and Bruno et al, dispersions comprising therapeutic and diagnostic agents having particle sizes as small as about 100 nm have been obtained on some occasions. However, for many applications, e.g., when further increased bioavailability and/or targeting to a specific tissue site is desired, it would be highly advantageous to produce dispersions free of unacceptable contamination having a particle size of less than 100 nm.

SUMMARY OF THE INVENTION

We have discovered that extremely fine particles, e.g., of a size less than 100 nanometers, of therapeutic and diagnostic agents free of unacceptable contamination can be prepared by milling in the presence of grinding media having a mean particle size of less than about 75 microns.

More specifically, in accordance with this invention, there is provided a method of preparing particles of a therapeutic or diagnostic agent which comprises grinding the agent in the presence of grinding media having a mean particle size of less than about 75 microns.

It is a particularly advantageous feature of this invention that there is provided a method of preparing extremely fine particles of therapeutic and diagnostic agents free of unacceptable contamination and/or discoloration.

Still another advantageous feature of this invention is that there is provided a method of fine grinding therapeutic and diagnostic agents, which method generates less heat and reduces potential heat-related problems such as chemical instability and contamination.

It is another advantageous feature of this invention that a method of fine grinding drugs and imaging agents is provided enabling improved pH control.

Other advantageous features will become apparent upon reference to the following Description of Preferred Embodiments.

DESCRIPTION OF PREFERRED EMBODIMENTS

This invention is based partly on the unexpected discovery that therapeutic and diagnostic agents can be prepared in extremely fine particles free of unacceptable contamination by grinding in the presence of extremely fine grinding media. While this invention is described herein in connection with its preferred utilities, i.e., with respect to therapeutic agents for use in pharmaceutical compositions and diagnostic agents for use in medical diagnostic compositions, it is also believed to be useful in other applications, such as the grinding of particles for cosmetic compositions, where extremely fine particle size is desired and contamination can be a concern.

In the method of this invention, a therapeutic or diagnostic agent is prepared in the form of submicron particles by grinding the agent in the presence of a grinding media having a mean particle size of less than about 75 microns.

In a preferred embodiment, the grinding media can comprise particles, preferably substantially spherical in shape, e.g., beads, of a polymeric resin. However, grinding media in the form of other non-spherical shapes are expected to be useful in the practice of this invention.

In general, polymeric resins suitable for use herein are chemically and physically inert, substantially free of metals, solvent and monomers, and of sufficient hardness and friability to enable them to avoid being chipped or crushed during grinding. Suitable polymeric resins include crosslinked polystyrenes, such as polystyrene crosslinked with divinylbenzene, styrene copolymers, polyacrylates such as polymethyl methylcrylate, polycarbonates, polyacetals, such as Delrin™, vinyl chloride polymers and copolymers, polyurethanes, polyamides, poly(tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like. The polymer can be biodegradable. Exemplary biodegradable polymers include poly(lactides), poly (glycolide) copolymers of lactides and glycolide, polyanhydrides, poly(hydroxyethyl methacrylate), poly (imino carbonates), poly(N-acylhydroxyproline)esters, poly (N-palmitoyl hydroxyproline) esters, ethylene-vinyl acetate copolymers, poly(orthoesters), poly(caprolactones), and poly(phosphazenes). In the case of biodegradable polymers, contamination from the media itself advantageously can metabolize in vivo into biologically acceptable products which can be eliminated from the body.

The polymeric resin can have a density from 0.8 to 3.0 g/cm$^3$. Higher density resins are preferred inasmuch as it is believed that these provide more efficient particle size reduction.

Furthermore, Applicants believe that the invention can be practiced in conjunction with various inorganic grinding media prepared in the appropriate particle size. Such media include zirconium oxide, such as 95% ZrO stabilized with magnesia, zirconium silicate, glass, stainless steel, titania, alumina, and 95% ZrO stabilized with yttrium.

The media can range in size up to about 100 microns. For fine grinding, the particles preferably are less than about 75 microns, more preferably, less than about 50 microns, and, most preferably, less than about 25 microns, in size. Excellent particle size reduction has been achieved with media having a particle size of about 5 microns.

The milling process can be a dry process, e.g., a dry roller milling process, or a wet process, i.e., wet-grinding. In preferred embodiments, this invention is practiced in accordance with the wet-grinding process described in U.S. Pat. No. 5,145,684 and European Patent Application 498,482. Thus, the wet grinding process can be practiced in conjunction with a liquid dispersion medium and surface modifier such as described in these publications. Useful liquid dispersion media include water, aqueous salt solutions, ethanol, butanol, hexane, glycol and the like. The surface modifier can be selected from known organic and inorganic pharmaceutical excipients such as described in U.S. Pat. No. 5,145,684 and can be present in an amount of 0.1–90%, preferably 1–80% by weight based on the total weight of the dry particle.

In preferred embodiments, the therapeutic or diagnostic agent can be prepared in submicron or nanoparticulate particle size, e.g., less than about 500 nm. Applicants have demonstrated that particles can be prepared having an average particle size of less than about 300 nm. In certain embodiments, particles having an average particle size of less than 100 nm have been prepared in accordance with the present invention. It was particularly surprising and unexpected that such fine particles could be prepared free of unacceptable contamination.

Grinding can take place in any suitable grinding mill. Suitable mills include an airjet mill, a roller mill, a ball mill, an attritor mill, a vibratory mill, a planetary mill, a sand mill and a bead mill. A high energy media mill is preferred especially when the grinding media is a polymeric resin. The mill can contain a rotating shaft. This invention can also be practiced in conjunction with high speed dispersers such as a Cowles disperser, rotor-stator mixers, or other conventional mixers which can deliver high fluid velocity and high shear.

The preferred proportions of the grinding media, the therapeutic and/or diagnostic agent, the optional liquid dispersion medium, and surface modifier present in the grinding vessel can vary within wide limits and depends, for example, upon the particular drug substance or imaging agent selected, the size and density of the grinding media, the type of mill selected, etc. The process can be carried out in a continuous, batch or semi-batch mode. In high energy media mills, it can be desirable to fill 70–90% of the volume of the grinding chamber with grinding media. On the other hand, in roller mills, it frequently is desirable to leave the grinding vessel up to half filled with air, the remaining volume comprising the grinding media and the liquid dispersion media, if present. This permits a cascading effect within the vessel on the rollers which permits efficient grinding. However, when foaming is a problem during wet grinding, the vessel can be completely filled with the liquid dispersion medium.

The attrition time can vary widely and depends primarily upon the particular therapeutic or diagnostic agent, mechanical means and residence conditions selected, the initial and desired final particle size and so forth. For roller mills, processing times from several days to weeks may be required. On the other hand, residence times of less than about 8 hours are generally required using high energy dispersers and/or media mills.

After attrition is completed, the grinding media is separated from the milled particulate product (in either a dry or liquid dispersion form) using conventional separation techniques, such as by filtration, sieving through a mesh screen, and the like.

The invention can be practiced with a wide variety of therapeutic and diagnostic agents. In the case of dry milling, the drug substances and imaging agents must be capable of being formed into solid particles. In the case of wet milling, the drug substances and imaging agents must be poorly soluble and dispersible in at least one liquid medium. By "poorly soluble", it is meant that the therapeutic or diagnostic agent has a solubility in the liquid dispersion medium, e.g., water, of less than about 10 mg/ml, and preferably of less than about 1 mg/ml. The preferred liquid dispersion medium is water. Additionally, the invention can be practiced with other liquid media. The therapeutic and diagnostic agents preferably are organic, crystalline materials.

Suitable therapeutic agents and classes of therapeutic agents are described in U.S. Pat. No. 5,145,684 and include Danazol, 5α, 17α,-1'-(methylsulfonyl)-1'H-pregn-20-yno[3, 2-c]-pyrazol-17-ol, camptothecin, piposulfam, piposulfan, naproxen and phenytoin. Other suitable drug substances include the NSAIDs described in PCT International Application PCT/US93/05082 published Dec. 23, 1993 and the anticancer agents described in European Patent Application 577,215 published Jan. 5, 1993.

Suitable diagnostic agents include derivatives of iodinated aromatic acids such as ethyl-3,5-bisacetoamido-2,4,6-triiodobenzoate (WIN 8883), ethyl(3,5-bis(acetylamino)-2,4,6-triiodobenzoyloxy acetate (WIN 12901), ethyl-2-(bis(acetylamino)-2,4,6-triiodobenzoyloxy)butyrate (WIN 16318), 6-ethoxy-6-oxohexyl-3,5-bis(acetylamino)-2,4,6-triiodobenzoate (WIN 67722). Other suitable imaging agents are described in U.S. Pat. No. 5,260,478, U.S. Pat. No. 5,264,610 and European Patent Application 498,482.

The following examples further illustrate the invention.

EXAMPLE 1

Effect of Media Size on Danazol Dispersion

A Danazol premix dispersion was prepared by combining 30% w/w Danazol (2–10 μm mean size powder), 10% polyvinyl pyrrolidone (PVP) having an average molecular weight of 15,000, and water. Polystyrene beads crosslinked with divinyl benzene (20% styrene, 80% divinylbenzene) were prepared by conventional polymerization techniques with mean diameters of 5, 25, 50, 200 and 450 microns. The 450 μm beads were added to the grinding chamber (300 ml, grade 316 stainless steel) of a Dyno-Mill (Model KDL-Special, manufactured by Chicago Boiler). A control dispersion was prepared by milling the premix dispersion for 120 minutes residence time. After milling, the control dispersion was diluted with water to a final concentration of 5% Danazol, 1.5% PVP and was further milled in a high energy attrition mill using the various sized polystyrene media for 60 minutes (recirculation time). The dispersion was separated from the media by 5 μm filtration, and the particle size measured by capillary hydrodynamic fractionation (CHDF) was as follows:

| Media Size (microns) | Weight Average Danazol Particle Size (nm) |
| --- | --- |
| Control | 149 |
| 450 | 105 |
| 200 | 86 |
| 50 | 80 |
| 25 | 92 (possible flocculation) |

These results indicate that particles having a mean size of less than 100 nm can be prepared in accordance with this invention.

EXAMPLE 2

Grinding with 5 Micron Size Media

In a subsequent experiment, the 5 micron polystyrene media described above was used under grinding conditions similar to those described above. The resulting dispersion particle size was 105 nm. It was entirely unexpected that excellent communition was achieved with such fine microscopic polymeric media. In aqueous solution, the 5 micron media appears as a milky solution to the unaided eye.

EXAMPLE 3

Continuous Milling Process Using Fine Polymeric Media in a 0.3 Liter DynoMill A premix dispersion was formed by combining micronized Danazol powder (2–10 μm mean size) with an aqueous PVP (avg. MW=15,000) solution at a ratio of 5.0% Danazol, 1.5% PVP and 93.5% water. 292 grams of this premix dispersion was combined with 379.6 grams of polystyrene crosslinked with divinyl benzene (20:80 w/w) milling media, nominal 50 micron size. This combined mixture was recirculated through a 0.3 liter DynoMill at 3200 rpm (100 cm$^3$/min) for 60 minutes (residence time). After milling, the media was separated using a 10 μm filter. After milling the particle size was measured by CHDF. The particle size distribution showed a weight average particle size of 35 nm.

EXAMPLE 4

Continuous Milling Process Using Fine Polymeric Media in a 0.6 Liter DynoMill A premix dispersion was formed by combining micronized Danazol powder (2–10 μm mean size) with an aqueous PVP (avg. MW=15,000) solution at a ratio of 5.0% Danazol, 1.5% PVP and 93.5% water. 2768 grams of this premix dispersion was combined with 3324 grams of polystyrene crosslinked with divinyl benzene (20:80 w/w) recirculated through a 0.6 liter DynoMill at 3200 rpm (100 cm$^3$/min) for 60 minutes residence time. After milling, the media was separated using a 10 μm filter. The particle size of this batch was not measured but microscopic examination indicated that the mean size was likely below 100 nm.

The invention has been described in detail with particular reference to certain preferred embodiments thereof, but it will be understood that variations and modifications can be effected within the spirit and scope of the invention.

We claim:

1. A method of grinding particles of a therapeutic or diagnostic agent, comprising grinding said agent in the presence of rigid grinding media having a mean particle size of less than about 100 microns, wherein the therapeutic or diagnostic agent particles produced by the grinding process have an average particle size of less than about 500 nm, and wherein the ground agent composition is free of unacceptable contamination caused by media deterioration.

2. The method of claim 1, wherein the therapeutic or diagnostic agent particles produced by the grinding process have an average particle size of less than about 100 nm.

3. The method of claim 1, wherein said method is a wet grinding process.

4. The method of claim 1, wherein said therapeutic agent is Danazol.

5. The method of claim 1, wherein said media have a mean particle size of less than about 75 microns.

6. The method of claim 5, wherein said media have an average particle size of less than about 50 microns.

7. The method of claim 6, wherein said media have an average particle size of less than about 25 microns.

8. The method of claim 7, wherein said media have an average particle size of about 5 microns.

9. The method of claim 1, wherein the rigid grinding media is a polymeric resin.

10. The method of claim 9, wherein said polymeric resin is polystyrene crosslinked with divinylbenzene.

11. The method of claim 9, wherein said polymeric resin is polymethylmethacrylate.

12. The method of claim 11, wherein said grinding takes place in a machine selected from the group consisting of a high shear disperser, a rotor-stator mixer, and a grinding mill.

13. The method of claim 12, wherein said grinding mill is selected from the group consisting of an airjet mill, a roller mill, a ball mill, an attritor mill, a vibratory mill, a planetary mill, a sand mill, and a bead mill.

14. A method of preparing particles of a therapeutic or diagnostic agent, comprising grinding said agent in the presence of rigid grinding media having a mean particle size of less than about 100 microns, wherein the therapeutic or diagnostic agent particles produced by the grinding process have an average particle size of less than about 500 nm, and wherein the ground agent composition is free of unacceptable contamination caused by media deterioration.

15. The method of claim 14, wherein the therapeutic or diagnostic agent particles produced by the grinding process have an average particle size of less than about 100 nm.

16. The method of claim 14, wherein said method is a wet grinding process.

17. The method of claim 14, wherein said therapeutic agent is Danazol.

18. The method of claim 14, wherein said media have an average particle size of less than about 75 microns.

19. The method of claim 18, wherein said media have an average particle size of less than about 50 microns.

20. The method of claim 19, wherein said media have an average particle size of less than about 25 microns.

21. The method of claim 20, wherein said grinding media have an average particle size of about 5 microns.

22. The method of claim 14, wherein the rigid grinding media is a polymeric resin.

23. The method of claim 20, wherein said polymeric resin is polystyrene crosslinked with divinylbenzene.

24. The method of claim 20, wherein said polymeric resin is polymethylmethacrylate.

25. The method of claim 14, wherein said grinding takes place in a machine selected from the group consisting of a high shear disperser, a rotor-stator mixer, and a grinding mill.

26. The method of claim 25, wherein said grinding mill is selected from the group consisting of an airjet mill, a roller mill, a ball mill, an attritor mill, a vibratory mill, a planetary mill, a sand mill, and a bead mill.

* * * * *